US005278325A

United States Patent [19]

Strop et al.

[11] Patent Number: 5,278,325

[45] Date of Patent: Jan. 11, 1994

[54] VEGETABLE OIL EXTRACTION PROCESS

[76] Inventors: Hans R. Strop, 12418 The Bluffs; Richard R. Perry, 10855 Meadow Trail, both of Strongsville, Ohio 44136

[21] Appl. No.: 559,702

[22] Filed: Jul. 30, 1990

Related U.S. Application Data

[62] Division of Ser. No. 271,002, Nov. 14, 1988, Pat. No. 4,944,954, which is a division of Ser. No. 855,127, Apr. 23, 1986, Pat. No. 4,808,426.

[51] Int. Cl.[5] .......... C07C 1/207

[52] U.S. Cl. .......... 554/12; 554/13; 554/15; 554/20; 554/21; 554/176; 554/188; 554/190; 554/195; 554/197; 554/204

[58] Field of Search .......... 260/412.6; 554/12, 10, 554/176, 13, 20, 21, 188, 190, 195, 197, 204

[56] References Cited

U.S. PATENT DOCUMENTS 4,698,185 10/1987 Dijkstra et al. .......... 554/176
4,808,426 2/1989 Strop et al. .......... 554/10

OTHER PUBLICATIONS

Hvolby, Chemical Abstracts, vol. 75, No. 25, pp. 221 & 222, 1971, 150529s.
Tanahashi et al., Chemical Abstracts, vol. 100, No. 13, p. 528, 1984, 101897m.
Dijkstra et al., Chemical Abstracts, vol. 105, #23 1986, 207838m.

*Primary Examiner*—Jose' G. Dees
*Assistant Examiner*—Deborah D. Carr
*Attorney, Agent, or Firm*—Fay, Sharpe, Beall, Fagan, Minnich & McKee

[57] ABSTRACT

A vegetable oil process and assembly is disclosed for extracting oil from an oil bearing material such as soybean, corn and the like. The process comprises adding at least one reagent to the oil bearing material to form a slurry mixture. The slurry is heated at a preselected temperature for a preselected period of time preferably under a partial vacuum. This processing reduces the phospholipid and trace metal content in the oil extracted from the oil heating material. The oil product produced is light in color, shows no turbidity and exhibits minimal amount of phosphorus, calcium, magnesium and iron. The oil is ready for physical refining.

20 Claims, 5 Drawing Sheets

VEGETABLE OIL EXTRACTION PROCESS

This is a divisional of co-pending application Ser. No. 271,002 filed on Nov. 14, 1988, now U.S. Pat. No. 4,944,954 which is a divisional of Ser. No. 855,127, filed Apr. 23, 1986, now U.S. Pat. No. 4,808,426.

BACKGROUND OF THE INVENTION

This invention relates to the art of oil extraction from a vegetable oil bearing material such as soybean, corn and the like, and more particularly, to a method and assembly for pretreating oil bearing vegetable material, extracting the oil therefrom, and producing a superior quality vegetable oil suitable for physical refining.

The invention is particularly applicable to the processing of oil from soybeans and corn germ, but is also applicable to many other vegetable oil bearing materials such as cottonseed, peanuts, sunflower seed, rape seed, fresh coconut meats or dried coconut meats, palm fruits and palm kernels and the like. The process of the present invention improves the extractability of the vegetable oils from the oil bearing materials while producing an oil product very low in phospholipids and in mineral content such as, specifically, calcium, magnesium and iron. The oil product is thus amenable to physical refining. However, it will be appreciated by those skilled in the art that the invention can be readily adapted for use with other extraction processes as, for example, where similar methods are employed to obtain other types of valuable constituent products.

Soybeans dominate the United States and world oil and vegetable protein markets and, accordingly, conventional vegetable oil processing techniques are predominantly directed to soy oil processing. Soy oil and soy protein offer maximum benefit to the consumer at a lower cost than can be obtained from any of the other major oilseeds.

A wealth of information exists describing the conventional methods and equipment used in vegetable oil processing. The commercially viable and successful techniques for soy oil processing entail a number of processing steps to extract the oil. Several techniques exist for the extraction of oil including solvent extraction, mechanical pressing, or a combination thereof, although the dominant technique in commercial use today is solvent extraction.

The crude oil extracted through these various known techniques is a dark colored, turbid liquid with an unacceptable odor and flavor. The liquid needs substantial further treatment to convert it to a bland, stable and nutritious product that is useful in the manufacture of shortening, margarine and salad and cooking oils. (Crude oils from other oilseeds are generally equally unacceptable as a food product and equally need to be further treated.) This further treatment consists of a number of steps which collectively may be called the refining process and which typically include such steps as degumming, neutralizing (alkali refining), bleaching and deodorization. Refining is necessary to remove phospholipids, free fatty acids, color bodies and other constituents which either affect efficient execution of any subsequent processing steps and/or affect the quality and the stability of the oil as a food product.

The crude oils produced by conventional solvent extraction and mechanical pressing methods from soybeans typically contain high levels of phosphorus compounds commonly called phospholipids, phosphatides, phosphoglycerides or gums in the range of 500 to 800 PPM (parts per million measured as phosphorus) and small but significant quantities of calcium, magnesium and iron. As much as 30% of the above phospholipids may be complexed with calcium and magnesium. These are commonly called non-hydratable phospholipids. In addition, it is generally known that prior methods of pretreatment and oil extraction of soybeans are, in fact, conducive to increasing the quantity of non-hydratable phospholipids present in the crude oils produced. The non-hydratable phospholipids generally require a separate degumming step in the refining process for their removal as will be discussed below. It is also well-known by those knowledgeable in the art of refining crude oils that the varying quantities of phospholipids in the crude oils may be attributed to variations in the extraction processes themselves and to the varying compositions of soybeans incurred during the growing, the harvest and the storage of the beans.

Since it is well-known that the presence of phospholipids and certain trace metals are undesirable to the quality of the final food grade vegetable oil, it is advantageous to reduce the level of these compounds as much as possible during the oil extraction processing.

The scope of processing steps referred to above, i.e. degumming, neutralization (alkali refining), bleaching and deodorization are often collectively called "refining." In a narrower use of the word "refining", it is often defined as the technique for neutralizing the free fatty acids in the oil. As this is done with alkali, the technique is also referred to as alkali refining, or because of the use of chemicals, as chemical refining. It should be kept in mind that each processing step generally affects more than one property of the crude oil. While neutralization primarily reduces free fatty acid levels, gums are also removed, the color may become lighter and some odor compounds may be removed. It is this propensity of a particular processing step to affect a variety of oil properties which makes it difficult to predict the complete cause and effect of the processing step and thus is accountable for the inconsistent results obtained from prior processing methods.

The typical known vegetable oil refining process involves several steps including a "degumming" step which essentially comprises adding water to the crude oil and heating and agitating the mixture for a period of time (approximately 10–30 minutes) and at temperatures of typically 50–70 degrees Centigrade. This mixture of hot oil and water is subjected to centrifugation wherein the water and oil are separated. In the process the hydrated phospholipids are separated with the water. The resulting partially "degummed" oil typically still contains a quantity of phospholipids, including all the non-hydratable phospholipids. This quantity may typically contain the equivalent to 10 to 120 PPM of phosphorus, however, this quantity varies depending upon the precise degumming techniques and conditions used.

The partially "degummed" oil produced in accordance with the above process may be further "degummed" to remove the non-hydratable phospholipids by the addition of certain chemicals (such as phosphoric acid) and water and by again heating and agitating the mixture followed by centrifuging. The "degummed" oil produced from this step will typically contain a quantity of phospholipids equivalent to 5–20 PPM of phosphorus.

The degummed crude oil from this second refining step is further subjected to several additional refining steps to remove other unwanted constituents such as the free fatty acids, the color bodies and other materials that contribute unwanted flavor, color and odor and which cause flavor reversion. These steps are more commonly identified as saponification of free fatty acids, washing of the oil to remove the soaps, neutralization and further washing to remove excess chemicals and soaps and further reduce the quantities of phospholipids, bleaching to remove color bodies and some additional quantities of phospholipids and, finally, deodorization. Oil produced from all of these extracting and refining steps is useful as a food product but still contains phospholipids equivalent to 1-10 PPM of phosphorus.

It should be particularly emphasized and noted in considering the subject invention that all of these prior known processing steps, and in particular the degumming steps, are applied to a crude oil product already extracted from the oil bearing vegetable material. The steps are not applied to the material itself but to the crude oil extracted from the material.

The capital cost associated with equipment to practice these refining steps is very high. Chemical refining involves many steps which are cumbersome, is captial intensive in that it requires substantial equipment which is hard to maintain such as centrifuges and filter presses, and is inherently characterized by oil losses as each of the refining steps produces a residue which carries with it a certain quantity of usable oil thus decreasing the yield of the salable food product oil.

Because of the high cost of equipment, the high operating expense and the losses of valuable product oil, there has been an emphasis and desire in recent years to practice a technique commonly called physical refining. In this technique a crude oil which has been subjected to several pretreatment processing steps is brought to an elevated temperature (250 degrees Centigrade or more) in a vessel or column operated under vacuum. Steam is sparged into the oil during treatment. Temperature and retention time conditions are selected such that the free fatty acids and other impurities and odiferous compounds are volatilized and distilled off. The treated oil is then typically cooled and given a post bleach to further lighten the color of the oil.

The capital cost and operating costs of a physical refining step is for many crude oils considerably less than that of chemical refining. Oil losses are also substantially less because only unwanted impurities are distilled off. Generally, very little post physical refining treatment is necessary to produce the finished shelf product. Hence, physical refining is very desirable to an oil processor.

However, a number of crude oils, including crude oils from soybean and corn germ extraction, require substantial pretreatment steps before the physical refining step can be applied. Most of these pretreatment steps are associated with the removal of hydratable and non-hydratable phospholipids from the crude oil.

Physical refining does not remove significant quantities of gums or phosphorus, nor does physical refining remove the heavy metals (such as iron). The presence of gums in excess of 6-20 PPM of phosphorus are subject to breakdown during physical refining due to the high temperatures employed and this causes unwanted flavor and color characteristics and causes acceleration of flavor reversion or rancidity (in the case of soy bean oil), as well as a reduction of oil stability (or shelf life) in other vegetable oils. The lower limits of the presence of phospholipids are not quite clear, but it is well known that there is a direct relationship of flavor reversion and loss of shelf life due to the presence of excessive quantities of phospholipids and or heavy metals such as iron in all vegetable oils. Therefore, the feed to a physical refining step should not contain a quantity of phospholipids measured in excess of 3-10 PPM measured as phosphorus. Those knowledgeable in the art may agree that high levels of phospholipids in the feed to the physical refining step cause deep set color changes in the oil which are hard to bleach out. The need for reduction of the phospholipid level in corn and soybean crude oils requires many of the prior art chemical refining steps described earlier and thus much or all of the economic incentive for physical refining is lost.

The application of physical refining is therefore limited to those vegetable oils that are naturally of such a quality as to have low limits of phosphorus (particularly the non-hydratable phospholipid form), have a low iron content and, in addition, contain a level of free fatty acids dictated by economic justification to permit the full application of physical refining or some modification thereof.

A major reason for not applying the physical refining step to soybean and corn oil crudes is that these crudes are high in phospholipids and in the case of corn oil contain much foreign solid matter such as finely divided starch particles. High levels of phospholipids in the crude affect the quality of the oil and generally limits have been set on the maximum phospholipid levels for physical refining of a crude oil. These requirements set by the refiners of crude oil range from less than 5 PPM (measured as P) to less than 20 PPM.

As noted above, the reduction of the quantities of phospholipids in soybean oil and corn oil crudes is not an easy task because part of the phospholipids are in a form generally referred to as non-hydratable phospholipids or may be converted to this form under the influence of certain constituents of the oilseeds or the oil. The greater part of the phospholipids generally referred to as hydratable phospholipids may be removed readily by contacting the crude with water, salt solutions, acidic or caustic solutions and the like and then removing the agglomerations of hydratable phospholipids by means of centrifuging. The removal of the non-hydratable phospholipids is more difficult. The non-hydratable phospholipids are complexes of calcium and magnesium with phospholipids and the known removal techniques depend upon chemical treatments to cleave the bond between the calcium and magnesium groups and the phospholipids, rendering the non-hydratable phospholipids into hydratable phospholipids and preventing reattachment of the calcium and magnesium group to the hydratable phospholipids.

The present invention contemplates a new and improved method and assembly which allows for the more efficient processing of a better quality oil product and meal product from a vegetable oil material.

As a result of the process according to the present invention the phospholipids substantially remain with the extracted solids. The extracted crude oil is very low in phospholipids and may be physically refined without any further pre-treatments.

BRIEF SUMMARY OF THE INVENTION

In accordance with the present invention, there is provided a method and assembly of extracting oil from an oil bearing material such as soybean, corn, and the like to allow for the more efficient processing of a better quality oil and meal product. The method comprises a series of steps. The first step can comprise pretreating oil bearing vegetable material to place it in a condition for mixing and grinding. These pretreating steps can comprise cleaning, drying, cracking or dehulling. The material can then be ground and mixed with a reagent for reducing the phospholipid content in the oil extracted. The reagent preferably comprises a reagent for cleaving the chemical bond of the non-hydratable phospholipids and thereby rendering the non-hydratable phospholipids into hydratable phospholipids. A complexing, precipitating or chelating agent can also be added to the mixture to prevent reversion of the hydratable phospholipids back to non-hydratable phospholipids.

The method also includes the step of adding an oil of preferably the same type as will be extracted from the oil bearing material to the mixture to form a slurry. Water can be added to the slurry to elevate the moisture content for deactivation of enzymes, bacteria and fungi, detoxification and pasteurization during a subsequent cooking step. After the slurry has been mixed with at least some of the above items, the slurry is cooked and agitated in a sealed cooker preferably under partial vacuum to allow for the completion of the above identified reactions. After cooking, some of the water can be evaporated and the resulting slurry is filtered or centrifuged to extract substantially all of the oil and produce a vegetable material cake. The oil produced by the extraction step is suitable for physical refining. The cake is further subjected to extraction steps for extraction of additional oil, then the cake is ground and dried for use as a protein metal.

In accordance with another aspect of the invention, a slurry is produced of vegetable oil material comprising a mixture of the oil bearing material, an oil preferably of the same type as oil to be extracted from the oil material and water to achieve a moisture level of at least 15% of the dry weight of the slurry. The slurry is cooked under a partial vacuum and in a reduced oxygen atmosphere to temperatures no higher than approximately 99 degrees Centigrade for a period of time. Oil is extracted from the slurry with known techniques to produce a crude oil containing a reduced level of phospholipids.

In accordance with a more limited aspect of the present invention, a third reagent, comprising a surfactant or protein reagent is added to the mixture.

In accordance with the present invention an improved oil and meal product is produced by the subject process.

In accordance with the present invention, an assembly is provided for extracting oil from an oil bearing material comprising a grinder for grinding the oil bearing material to a preselected particle size, a mixer for mixing the material with a reagent for reducing the quantity of phospholipids in the extracted oil, and an oil of preferably the same type as will be extracted from the oil bearing material to form a slurry, a cooker for cooking the slurry for a preselected period of time at a preselected temperature to insolubilize the proteins in the slurry and for hydrating the phospholipids in the slurry, a separator for extracting the oil from the slurry to leave an oil soaked cake and, a separator for extracting the oil from the oil soaked cake.

One benefit obtained by use of the present invention is a vegetable oil extraction process which provides for the extraction from an oil bearing material of an oil low in phospholipids and trace metals. The oil produces a superior quality vegetable oil suitable for direct physical refining. The oil is lighter in color and more bland, stable and nutritious than that produced by prior known crude oil production processes. The oil is so superior that many known chemical refining steps are obviated.

Another benefit of the subject invention is a pretreatment process for vegetable oil material which includes grinding the material in the presence of a hot oil of the same type as will be extracted to condition the oil bearing material to release oil with a much lower energy requirement for subsequent oil extraction steps. Lower energy requirements in the oil extraction steps minimize heat requirements and heat production (for example in screw pressing) and accordingly allows for less heat damage to the oil product.

Another benefit obtained from the present invention is a process which substantially reduces the number of processing steps necessary to produce a physically refinable oil and, the oil losses inherently suffered by prior known methods which involve a greater number of processing steps. The process reduces the capital equipment requirements over prior known processing methods and assemblies.

Another benefit of the subject invention is an oil processing method which produces a vegetable oil product of substantially low and uniform levels in phospholipids regardless of the varying content of phospholipids in the vegetable oil material.

Still another benefit of the subject invention is a chemical process and assembly which chemically refines a vegetable oil material slurry prior to extraction of the oil from the oil bearing material.

Yet another benefit of the subject invention is a pretreatment process for corn germ and soybean which includes evaporating water contained in the germ and seed under controlled conditions of temperature, vacuum and retention time in the evaporator to further condition the oilseed matrix and improve the releasibility of the oil from the oilseed matrix during subsequent extraction steps such as centrifuging and pressing.

Another benefit is that during the practice of the invention, oil and meal in the process are subjected to only low temperatures and pressures for short periods of time resulting in minimal heat damage to both oil and meal. For known conventional processing operations, including full pressing, pre-press solvent extraction and direct solvent extraction, the temperatures to which the oil and meal are exposed may reach 230–310 degrees F. (110–154 degrees C.), resulting in deep red color and other heat damage to the oil. In the process of the subject invention, temperatures are typically no higher than 210 degrees F. (99 degrees C.).

Yet another benefit of the subject invention is that temperature and moisture conditions throughout the system are such that the hydratable phospholipids stay with the cake or meal product of the process and thus the oil from the process is substantially free of hydratable phospholipids. The temperature and moisture conditions prevent the conversion of hydratable phospholipids into non-hydratable phospholipids. Suitable reagents may be added in the system to convert non-hydratable phospholipids into hydratable phospholipids and thereby facilitate the phospholipid removal.

Yet another benefit of the subject invention is the production of an oil through a washing and filtering step which removes substantially all phospholipids, calcium, magnesium and trace metals and in the case of corn oil, substantially all starches. The oil produced from the washing and filtering step is ready for physical refining.

A further benefit of the present invention is an assembly which lends itself to a reduced oxygen atmosphere processing. If desired, the oil can be processed in a nitrogen or other inert gas atmosphere when the oil is at an elevated temperature. The equipment may be fabricated to sanitary standards, manufactured of stainless steel, and lends itself to the clean-in-place techniques used in the food and dairy industry.

Yet a further benefit of the present invention is a process which includes a physical refining step operated at an elevated temperature. To avoid the substantial waste of heat, heat used in the physical refining step may be integrated with the lesser heat requirements of pre-physical refining processing steps to produce a more energy efficient oil processing operation.

Other benefits and advantages for the subject new vegetable oil extraction process will become apparent to those skilled in the art upon a reading and understanding of this specification.

BRIEF DESCRIPTION OF THE DRAWINGS

The invention may take physical form in certain parts and arrangements of parts, and in certain steps and arrangements of steps, the preferred and alternative embodiments of which will be described in detail in this specification and illustrated in the accompanying drawings which form a part hereof and wherein.

DETAILED DESCRIPTION OF THE INVENTION

Figure 1:
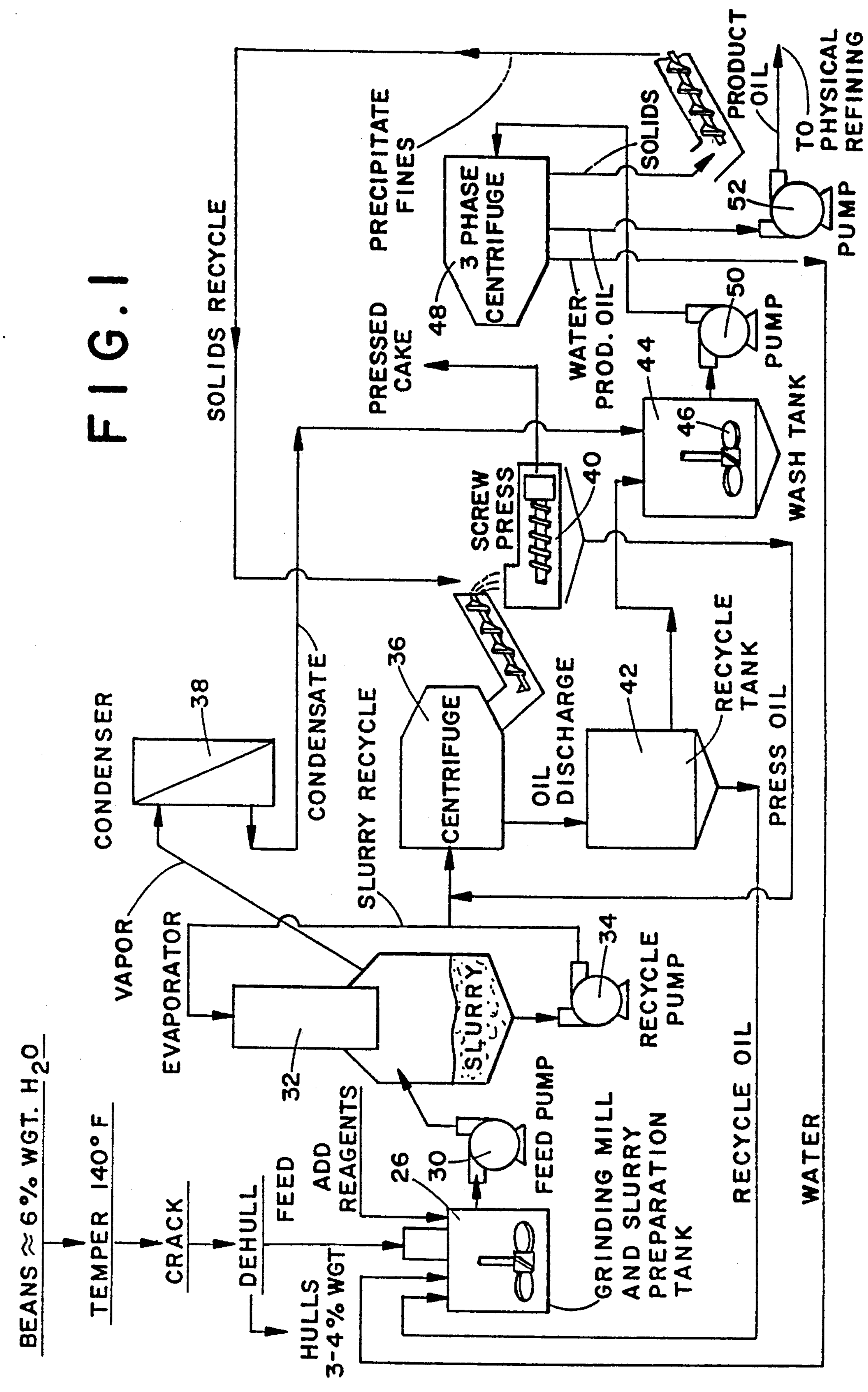
FIG. 1 is a schematic diagram of a plant formed in accordance with the present invention for extracting oil from an oil bearing material such as soybeans.

Referring now to the drawings wherein the showings are for purposes of illustrating the preferred and alternative embodiments of the invention only and not for purposes of limiting same, the Figures show a vegetable oil extraction process and assembly for the production of a superior quality vegetable oil product suitable for physical refining. Although, as noted above, the invention is applicable to a wide variety of vegetable oil bearing materials, its predominate commercial concern is directed to soybean and corn and will be particularly discussed with reference to these oil bearing materials.

Figure 3A:
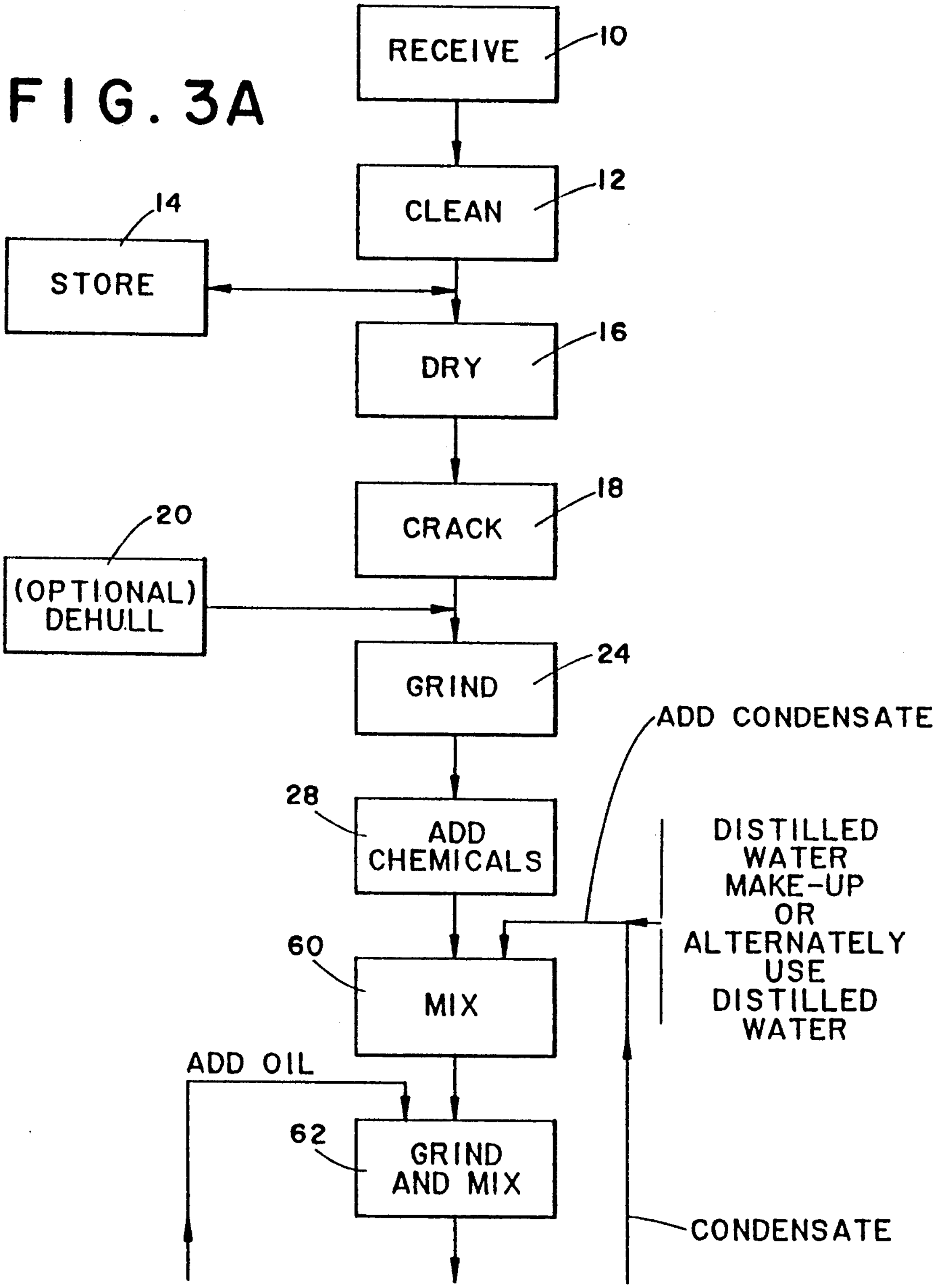
FIGS. 3A and 3B comprise a block diagram illustrating the process steps in the practice of the present invention in extracting oil from a vegetable oil material such as soybeans; and, FIG. 4 is a block diagram illustrating the steps of a process in accordance with the present invention for extracting oil from an oil bearing material such as wet corn germ, dry corn germ or wet/dry germ mixtures.
Figure 3B:
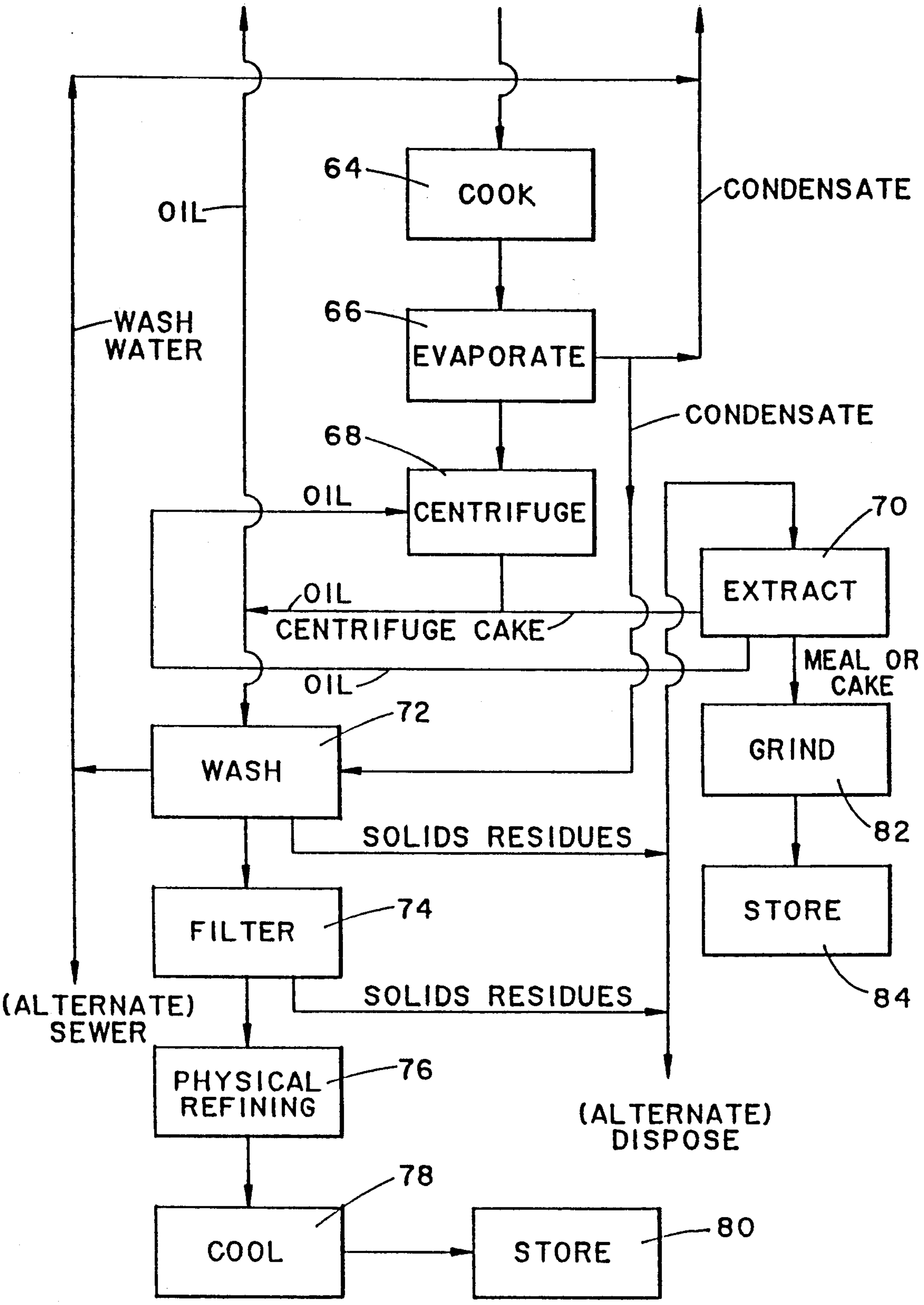

With reference to FIGS. 1, 3A and 3B, the invention, as it is applicable to soybeans is specifically illustrated. The first processing step for a harvested soybean delivered to a processing plant comprises receiving 10 and cleaning 12. Thereafter, the beans may be stored as at 14 or transmitted for further processing. Storage of the beans generally results in higher phospholipid levels in the beans due to changes in bean compositions during the storage period.

Beans in storage are dried to have a typical moisture content of about 6% by weight. Further processing for oil extraction can entail drying or tempering as at 16, cracking as at 18, and dehulling as at 20 using equipment commonly used for these purposes and known to those knowledgeable in soybean processing. The drying typically occurs at a temperature of 220–240 degrees F. (104–116 degrees C.) or lower to minimize heat damage to the beans. Dehulling typically removes approximately 3–4% of the weight of the conditioned material. Dehulled beans are next comminuted or ground as at 24 in a dry state to produce a ground bean material suitable for mixing in a grinding mill and slurry preparation tank 26 (FIG. 1).

A mixture is formed in the slurry preparation tank 26 comprised of several items. In the preferred form of the invention, several chemical reagents are added as at 28. These reagents may be introduced dissolved in water. Also, additional water may be introduced. Typically, the total water added may comprise 15 weight percent of the dry weight introduced in the case of soybeans. In a preferred embodiment of the invention, the slurry preparation tank 26 is also a cooking vessel in which the soybean particles may be cooked or partially cooked, that is, heated for a period of time to an elevated temperature in the presence of the water introduced. In this cooking step enzymes, bacteria and fungi are deactivated and the oil and the solids are detoxified and pasteurized. Among the enzymes deactivated are urease, various protreases and lipases and the enzyme which promotes the conversion of hydratable phospholipids into non-hydratable phospholipids. Preferably, a first reagent is added to reduce the phospholipid content in the oil extracted from the soybeans. The first reagent may be an acid. The non-hydratable phospholipids in soybeans are substantially magnesium and calcium phosphatidates which upon treatment with an acid are acidulated and converted into a disassociated phosphatidic acid, which disappears from the oil phase in the form of micelles in the water phase or in hydrated form as liquid crystals. In other words, the magnesium and calcium bonds linking the non-hydratable phospholipids to the oil (lipids) are ruptured by the acid and the non-hydratable phospholipids thus become hydratable. The resulting magnesium and calcium complexes separate from the oil phase and are now in the water phase. When this happens, certain salt complexes may be formed. The salt complexes may be in several forms in the water phase, that is, as a precipitate, in suspension, in solution or in the form of a micelle.

However, this hydration or rupturing reaction is reversible. As the water evaporates, the disassociated non-hydratable phospholipids may return to the solution in the oil as non-hydratable phospholipids. Thus, precipitating, chelating, blocking or binding agents can be added, as explained more fully below, to prevent the reverse reaction. Preferably, the reagent used for rupturing of these chemical bonds comprises phosphoric acid ($H_3PO_4$). Alternatively, a reagent from the following group could be employed: Citric acid ($HOOCCH_2$-$C(OH)(COOH)CH_2COOH$—$H_2O$), hydrochloric acid ($HCl$), potassium chloride ($KCl$), sodium chloride ($NaCl$), sodium hydroxide ($NaOH$), disodium hydrogen phosphate ($Na_2HPO_4$), potassium dihydrogen phosphate ($KH_2PO_4$), acetic anhydride $(CH_3CO)_2O$, sulfuric acid ($H_2SO_4$), sodium borate ($Na_2B_4O_7$), and glycine ($NH_2CH_2COOH$).

The degree of rupturing of the appropriate chemical bonds increases with increasing contact between the oil and the water phase. Accordingly, in the grinding mill and slurry preparation tank 26, the ground soybean are comminuted and homogeneously mixed with the slurry so that the ground soybeans are ground to a preselected particle size which facilitates the desired chemical reaction in the heating step as will be in hereafter more fully explained.

Since it is known that the above hydration reaction is reversible, it is necessary to lock-out the reversible reaction. Accordingly, a precipitating, binding, blocking or chelating reagent can also be mixed into the grinding mill to ultimately sequester the trace metals and/or bind the salt complexes to something else. The binding reagent preferably comprises sodium citrate ($C_6H_5O_7Na_3$—$2H_2O$), but may also comprise sodium chloride (NaCl), sodium acetate ($NaC_2H_3O_2$), sodium sulfate ($Na_2SO_4$), sodium hydrogen sulfate ($NaHSO_4$), trisodium phosphate ($Na_3PO_4$), EDTA ((ethylenediaminetetraacetic acid, (($HOOCCH_2)_2$ $NCH_2CH_2N(CH_2COOH)_2$)), sodium floride (NaF), sodium-oxalate ($Na_2C_2O_4$), sodium-tartrate ($Na_2C_4H_4O_6$—$2H_2O$), sodium carbonate ($Na_2CO_3$) and sodium pyrophosphate ($Na_4P_2O_7$).

In addition, again as the water is evaporated, the acidity of the remaining water and slurry changes and thus certain water insoluble precipitates may return to the solution. Certain reagents under certain conditions comprising surfactants (anionic, cationic, nonionic) or proteins are added to the mixture to control to some extent the degree of acidulation. Preferably, the surfactant or protein agent is selected from the group consisting of ethoxylated fatty alcohol, oleylamine, casein, pancreatin, soy protein and Na-soap.

In the preferred practice of the invention, all of these reagents are added in the grinding mill. However, it is within the scope of the invention to add only the first and second reagents, the first reagent only, or no reagents at all and still produce an improved product oil.

Also added in the grinding mill 26 is a portion of oil of preferably the same type as will be extracted from the oil bearing material to form a pumpable slurry. It is within the scope of the invention to employ an oil other than that of the same type as will be extracted from the oil bearing material. Oftentimes an oil blend is desired in which case another type of oil, either vegetable or animal, may be employed.

The treatment of the oil bearing material by grinding in the presence of hot oil conditions the oilseed to release oil with a much lower energy requirement in the later oil extracting steps such as centrifuging and screw pressing. This lowered energy requirement in the extracting steps means that less horsepower is required per ton of seed being processed and thus less heat damage is done to the product oil.

Also added to the mixture in the grinding mill is water to achieve a moisture level of at least 15% of the dry weight of the slurry in the slurry preparation tank. The addition of water is desirable so that the slurry can be properly cooked at a later processing step.

With continued reference to FIG. 1, it is noted that the oil and water added to the slurry preparation tank is obtained through system recycle operations.

In one commercial embodiment of the invention, the slurry preparation tank level is controlled such that under steady state conditions a ratio of preferably 2.5 weight parts of recyled oil to 1 weight part of soybean solids (bone dry basis) is maintained. To the slurry is added 10-30 weight percent of water based upon the weight of dry soybean solids introduced. As noted before, this water may be condensate from other plant processing steps, with or without demineralized or distilled water makeup. The various liquid or solid reagents comprising acids, bases, salts and others which are added to the slurry preparation tank 26 are added to enhance the quality of the end product oil with an emphasis on phospholipid and trace metal removal. One desirable system of additives is one pound per hour (0.454 kg/hr) of concentrated (85%) phosphoric acid and one pound per hour (0.454 kg/hr) of sodium citrate per 1,700 pounds per hour (772 kg/hr) of soybean solid feed. The slurry preparation tank is continuously agitated to promote wetting of the soybean solids by water and to promote proper dispersion of the reagents. The temperature of the slurry in the tank, without any external application of heat, is approximately 150 degrees F. (66 degrees C.) and follows from the mass flow rate, specific heat and temperature of the soybean solid food, the recycle oil stream and recycle water (condensate) and make-up water steams. A function of the slurry preparation tank is to provide a degree of cooking to the soybean solids and to partially or wholly deactivate all enzymes affecting such properties as the stability of the oil and meal and the enzyme or enzymes which control the conversion of hydratable phospholipids to non-hydratable phospholipids and to detoxify and sterilize said oil and meal. The degree of cooking depends upon both temperature and retention time of the solids in the tank. The temperature can be increased by applying external heat to the tank. Maximum temperature of the slurry in the slurry preparation tank could match the maximum temperature in the evaporator pump described below (typically 185-210 degrees F., 85-99 degrees C.). The maximum retention time in the slurry preparation tank 26 may be established by the design of the tank.

Another function of the slurry preparation tank 26 is to condition the soybean solids for the release of oil in the subsequent processing steps and the extraction steps in the centrifuge and the screw press.

Yet another function of the tank 26 is to provide an enclosure for operation in a reduced oxygen atmosphere by introduction of a nitrogen or other inert gas atmosphere.

The slurry is pumped through a sizing mill (not shown) which preferably should be a Reitz disintegrator or equivalent. The mill should include a screen such that a desirable particle size distribution is achieved, typically 10 weight per cent plus 20 mesh; 82 weight percent plus 40 mesh. A feed pump 30 feeds the sized slurry to a falling film evaporator 32.

The evaporator 32 is operated under vacuum conditions (for example, 25 inches of mercury or 635 millimeters of mercury) to limit temperature exposure of the oil in the system. The evaporator is preferably operated in combination with the recycle pump 34 to promote proper film formation in the tubes of the evaporator heat exchanger and to insure optimum heat transfer conditions. The evaporator sump temperature is typically 185-210 degrees F. (85-99 degrees C.); the vapor temperature is approximately 150 degrees F. (66 degrees C.). The evaporator sump is sized such that retention time in the evaporator 32 may be controlled to between 20 and 40 minutes.

One function of the evaporation is to remove substantially all of the water introduced in the slurry preparation step with the soybean feed and the recycled condensate and make-up water streams. A small amount of water in the soybean solids must remain for effective separation of oil from the solids in the centrifuge and the screw press.

Another function of the evaporator 32 is to complete if necessary, the cooking initiated or partially completed in the slurry preparation tank 26, i.e. complete the deactivation of enzymes and the detoxification and sterilization of the oil and meal.

Still another function of the evaporator 32 is to complete the beneficial reactions between the reagents and the phospholipids initiated in the slurry preparation tank 26.

Yet another function of the evaporator 32 is to complete the conditioning of the soybean solids to improve the release of oil from the solids in the extraction step in the centrifuge and the screw press. The dried slurry is discharged to a high gravity decanter centrifuge 36 such as may be commerically obtained from the Sharpless Division of Pennwalt Corporation, Philadelphia, Pa. and from other centrifuge manufacturers. The solids in the feed to the centrifuge should contain 3–4 weight percent of moisture on an oil-free solids basis. Water condensed from the evaporator 32 in condenser 38 is employed in later processing steps.

The solids obtained from centrifuge 36 are commonly referred to as centrifuge cake and will contain 25–35% oil by weight. The cake is conveyed to a screw press 40 wherein the solids are pressed to a 3–4 weight percentage of residual oil in the press cake.

Because of the pretreatment of the soybean solids in the slurry preparation tank and grinding mill 26 and in the evaporator 32, the screw press 40 requires substantially less power to press out the oil (typically 1.5 hp metric ton per day instead of the 4 hp metric ton per day required for pressing soybeans in the conventional solvent extraction pretreatment technique). The cake from the process is a very light tan colored product. The oil from the screw press 40 is conducted to the feed stream to the centrifuge 36 in order to remove press fines from the press oil stream. The oil from the discharge of the centrifuge is conducted to a recycle tank 42 for either return to the slurry preparation tank 26 or as product oil which is communicated to a wash tank 44. The temperature of oil in the recycle tank is approximately 185–200 degrees F. (85–93 degrees C.). The product oil from the recycle tank 42 typically contains 1–2 ppm (parts per million) of phospholipids (measured as elemental phosphorus) and trace metals such as calcium, magnesium and iron. The product oil is communicated from the recycle tank 42 to the wash tank 44 in which distilled water or condensate is introduced. The wash tank is agitated with an agitator 46. The wash tank 44 is sized for a retention time of oil and water of at least five minutes. The oil and water mixture from the wash tank is pumped to a centrifuge 48 by a pump 50. The centrifuge 48 may comprise a three phase high gravity horizontal decanter centrifuge as is commercially available from the Sharpless Division of Pennwalt Corporation, Philadelphia, Pa. or a high gravity disc centrifuge such as is available from Alfa Laval Corporation of Tumba, Sweden or Westphalia Corporation, West Germany. The water phase separated in the centrifuge 48 is returned, if necessary with makeup distilled water, to the slurry preparation tank 26. The wet solids discharge from the centrifuge 48 which contains the phospholipids, various soaps, starches and solids of unknown composition may be disposed or added to the feed of the screw press 40. The product oil is typically filtered from the centrifuge and pumped by pump 52 to a physical refining assembly (not shown). The product oil from the centrifuge 48 shows no turbidity and there is no detectable content of phosphorus, calcium, magnesium and iron. The oil is ready for physical refining.

With particular reference to FIGS. 3A and 3B, the method employed in the assembly of FIG. 1 is illustrated. After the soybeans have been ground or comminuted as indicated by the grinding step at block 24, the mixture is fed to the grinding mill and slurry preparation tank. The reagents are added as indicated by block 28 and mixed with water at block 60. The water may comprise condensate from the evaporator at block 66, or from the wash water at block 72 with demineralized or distilled water makeup or, alternatively, an independent deminearlized or distilled water source may be employed. Before grinding step 62, an oil of preferably the same type as the oil to be extracted from the oil bearing material is added to the slurry to facilitate the grinding step and to produce a pumpable slurry. The oil is preferably a recycled oil obtained from the centrifuge 36. The mixture preferably has a moisture level of at least 15% of the dry weight of the slurry. Providing a suitable moisture level in the slurry is important to enable the necessary cooking of the slurry in a low pressure, low temperature environment. The slurry is next cooked or heated as at 64 in the slurry preparation tank 26 and in the evaporator 32 (FIG. 1).

The cooking step accomplishes several results. First, it allows for the first reagent to rupture the magnesium and calcium bonds linking the non-hydratable phospholipids and thus rendering them hydratable; second, it allows the second reagent (the precipitating, binding or chelating reagent) to bind the resulting magnesium and calcium complexes to lock-out the reversion of the phospholipids into a non-hydratable form and consequently also reduce the trace metal content in the oil ultimately extracted from the slurry; third, it allows for the deactivation of the naturally occurring enzymes such as lipase and urease or other enzymes which may be toxic or cause toxic products to form in the slurry or which may control the conversion of hydratable phospholipids into non-hydratable phospholipids; fourth, it provides sterilization or pasteurization of the slurry to deactivate certain bacteria and fungi; and, fifth, it substantially insolubilizes proteins in the slurry. It should be noted that in order to accomplish enzyme deactivation, pasteurization, rendering selective fungi and microorganisms harmless and toxic destruction, the slurry must be cooked for a preselected time at a preselected temperature with a preselected moisture content. It has been experimentally found that the invention may be successfully practiced by cooking under a partial vacuum and in a reduced oxygen atmosphere at temperatures no higher than approximately 99 degrees C. (210 degrees F.) for a time preferably within a period of 20–40 minutes. Not only does such a low temperature/low pressure cooking operation accomplish the desired results, but it also avoids damage caused by the conventionally used higher temperatures to the ultimately resulting oil and meal products.

After the slurry has been properly cooked, it is subject to evaporation 66 where water condensate is removed from the slurry for communication back to the slurry preparation tank 26 or the oil discharge wash tank 44. The partially evaporated slurry is next communicated to a centrifuge 36 (FIG. 1) for oil and solid phase separation by the step of centrifuging 68. The solids or centrifuge cake generally contains 25–35% oil by weight which is extracted as at 70 typically by pressing. The oil discharge from the extracting step is conducted to the feed stream of the centrifuging step 68 in order to remove press fines from the press oil stream. The product oil from the centrifuge is a substantially improved crude oil product which typically contains only 1–2 ppm of phospholipids (measured as phosphorus) and a minimal amount of trace metals such as calcium, magnesium and iron. The product oil is washed as at 72 with distilled water or condensate, filtered as at 74 or centrifuged for separation of the water and solids residue from the oil, physically refined as at 76, cooked as at 78, and ultimately stored as at 80. The wash water and solids residue separated from the oil in the washing and filtering steps may be sewered or disposed; alternatively, the wash water may be fed back to the mixing step 60 which can take place in the slurry preparation tank 26 (FIG. 1). The wash water can be filtered and thus demineralized water could be fed back to the slurry preparation tank. The wash water is also advantageous since it retains heat and thus reduces the energy requirements for the treatment process. As noted above, the finished product oil shows no turbidity and there is a very low content (usually less than 1 PPM) of phosphorus and generally no detectable content of calcium, magnesium and iron.

The metal cake obtained from the extracting step 70 is a high protein useful meal product which can be ground as at 82 to a commercially salable product, dried and stored as at 84.

EXAMPLES FOR SOYBEANS

The following bench scale examples were performed to prove the subject invention.

Four hundred grams (dry basis) of soybeans were obtained from a conventional soybean processor company and cleaned, cracked and partially dehulled. The soybeans are commercially available from Cargill Inc. of Decatur, Ill. or other suppliers. The approximate properties of the soybeans were as follows:

19.8% oil on a 10% moisture basis
4730 PPM phospholipids as elemental phosphorus (P)
11.92% moisture The oil in these soybeans when extracted with hexane (a commercial solvent) typically contained:

1.2% Free Fatty acid (FFA)
0.25% moisture
597 PPM of P

The above soybeans were mixed into 1200 ml of semi-refined soybean oil commercially available from the Procter and Gamble Company, Inc. Cincinnati, Ohio and other suppliers. The approximate properties of this oil were as follows:

0.3% FFA
0.7 Red (Lovibond scale)
3.0 PPM of P

The mixture (or slurry) was introduced into a heavy duty "Waring" type blender of the type commercially available from Vitamix Corporation of Olmsted Falls, Ohio under the trade name of VITAMIX 3600. The slurry was mixed at the lowest speed setting for five minutes.

The mixed and ground slurry was then introduced into a flask. After the flask was sealed the mixture was agitated with a laboratory agitator at 180 RPM. A vacuum of approximately 29 inches of mercury (737 millimeters of mercury) was pulled on the flask. The flask and the contents were immersed in a constant temperature water bath maintained at approximately 99.5 degrees C. The flask was connected to a laboratory glassware condenser and water was evaporated from the slurry.

The batch of ground soybeans and soybean oil would boil at approximately 68–75 degrees C. and the temperature would remain level at approximately 68–75 degrees C. until a substantial portion of the water had been evaporated. At that point, the temperature would start to rise sharply and asymptotically approach the temperature of the water bath. When the temperature reached approximately 85–90 degrees C., the vacuum was broken and the slurry sample was poured into a Buechner funnel lined with filter paper (Watman No. 5).

The filtered oil was collected in a flask. The oily filter cake, containing approximately 45–50 weight percent of oil was put in a press cage in which the ram of a Carver hydraulic laboratory press moved to compress the oily cake to a degree wherein the remaining press cake would only contain approximately 10 weight percent of residual oil. The oil separated from the cake was mixed with the filtered oil. A typical sample of the oil showed:

2.5% FFA
3.0 to 3.5 Red (Lovibond scale)
230 PPM of P

The test was repeated several times using the oil from each preceeding test, but new samples of 400 grams of soybeans were introduced each time. Since in each test the 400 grams of soybeans contained approximately 80 grams of oil and as the press cake still contained 27 grams of oil at 9.15 weight percent, the original soy oil was diluted with 53 grams of new oil originating from the soybeans. Thus, to replace the original oil sample of 1200 ml (1080 grams) multiple tests similar to the above are required until the phosphorus content asymptotically approached that of the oil in the soybeans used. After seven cycles as described above the P in PPM was 627.

The above oil sample was used as a "bench mark" to determine the number of cycles required in the practice of the invention hereinafter described. Four hundred grams of the above soybeans were used, to which 1200 ml of the above commercially available semi-refined oil was mixed in the VITAMIX blender previously described and the mixture was subjected to mixing and grinding at the high speed setting for 10 minutes. Three grams of concentrated (85%) phosphoric acid was added at the onset of the mixing. Subsequently, (after 2 minutes) three grams of laboratory grade sodium citrate was added to 40 ml of distilled water. The solution was added to the mixing slurry and the mixing was continued for an additional 8 minutes. The mixed and ground slurry was introduced to an agitated flask. The flask was sealed and approximately 5 inches of mercury (127 millimeters of mercury) was pulled on the flask. The mixture was heated to 90 degrees C. and maintained at that temperature for 20 minutes. Then the vacuum was increased to approximately 29 inches of mercury (737) millimeters of mercury) vacuum. The water bath temperature was maintained at approximately 99 degrees C.

The batch of soybean and soybean oil would boil at 68–75 degrees centigrade. The temperature would remain level at approximately these temperatures until a substantial portion of the water was evaporated. At that point the temperature would rise sharply and asymptotically approach the temperature of the water bath.

When the temperature reached approximately 85 degrees to 90 degrees centigrade, the vacuum was broken and the slurry sample was poured into a Buechnet funnel lined with filter paper (Watman No. 5).

The filtered oil was collected in a flask. The oily filter cake, containing approximately 45 to 50 weight percent of oil, was put in a press cage in which the ram of a Carver hydraulic laboratory press moved to compress the oily cake to a degree wherein the remaining press cake would only contain 10 weight percent of residual oil. The oil separated from the cake was mixed with the filtered oil. A typical sample of the oil showed:

0.8% FFA

3 Red (Lovibond scale)

1-2 PPM of P (phospholipids)

The test was repeated until the original sample had substantially disappeared and had been replaced by oil from the subsequent quantities of soybeans introduced. It was found in the series of tests that the free fatty acid content and the red color (Lovibond scale) would asymptotically approach the free fatty acid content and the red color of the oil in the soybeans, i.e. approximately 1.2% FFA and 3 Red. However, the phospholipid content of each subsequent oil sample would stay constant within a range of approximately 1 to 2 PPM of P.

A 1000 ml sample of the soybean oil from the above tests was washed with 50 ml of distilled water and the mixture was intensively mixed and heated to 70 degrees C. for 10 minutes under 5 inches (127 mm) of vacuum. After mixing the oil it was centrifuged in a laboratory centrifuge for 10 minutes at 6000 times gravity. This centrifuging substantially removed all of the water. A whitish-brown solid precipitate was formed in the water and the precipitate was judged to be iron, calcium and magnesium complex salts. The oil had some turbidity which disappeared at the 60-70 degrees centigrade range.

The oil sample was cooled to 50 degrees centigrade and filtered in a Beuchner funnel with Watman No. 5 filter paper.

The washed, centrifuged and filtered oil sample was no longer cloudy and the content of P was judged to be in the 0 to 0.5 PPM range (AOCS Official Method Ca 12-55 ).

The wash water contained 35 PPM of phosphorus.

Also, the oil sample did not show any detectable content of calcium, magnesium, iron or other trace metals.

Washing samples from other tests in the test series showed no statistically significant departure of the test results from the earlier wash test, i.e. phospholipids measured as phosphorus were barely detectable (0 to 0.5 PPM range) and trace metals such as calcium, magnesium and iron could not be detected.

A 1000 ml sample of the above washed oil was introduced into a laboratory bench scale physical refining assembly which was operated under 29.5 inches of mercury vacuum (750 mm). The sample was heated to 252 degrees C. (485 degrees F.) and high temperature steam was sparged into the oil sample through a special steam dispenser. The sample was subjected to this physical refining treatment for 6.5 hours. The sample was then cooled and judged to contain the following:

0.01-0.02% FFA 0.00 PPM phosphorus 0.5 Red (electronic color meter)

0.0 Peroxide value 0.002% Moisture

In another series of tests the sodium citrate reagent was replaced with 3 grams of sodium sulphate and processed as before. Oil samples from this test showed an average of 1.0-2.0 PPM of phosphorus.

In another series of tests the phosphoric acid reagent was replaced with 3 grams of acetic anhydride and the sodium citrate reagent was replaced with sodium acetate.

In still another series of tests the phosphoric acid reagent was replaced with mono-hydrated citric acid crystals.

In all these series the tests with the various reagents, the oil samples contained an average of 1.5-3.0 PPM of phosphorus. However, when washed with 50 cc of distilled water the phosphorus content was judged to be less than 1 PPM.

Figure 2:
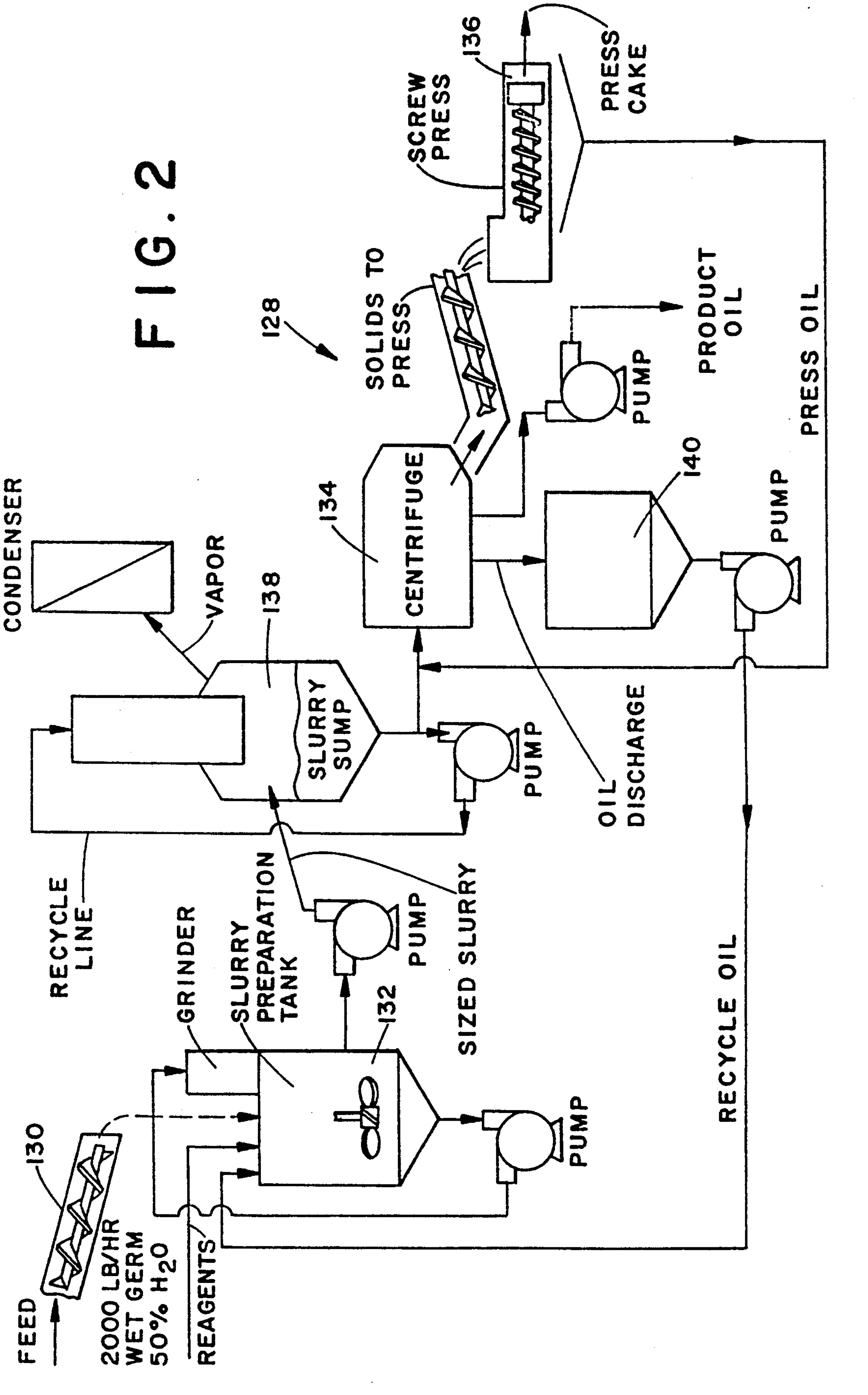
FIG. 2 is a schematic diagram of a plant formed in accordance with the present invention for extracting oil from an oil bearing material such as corn germ.
Figure 4:
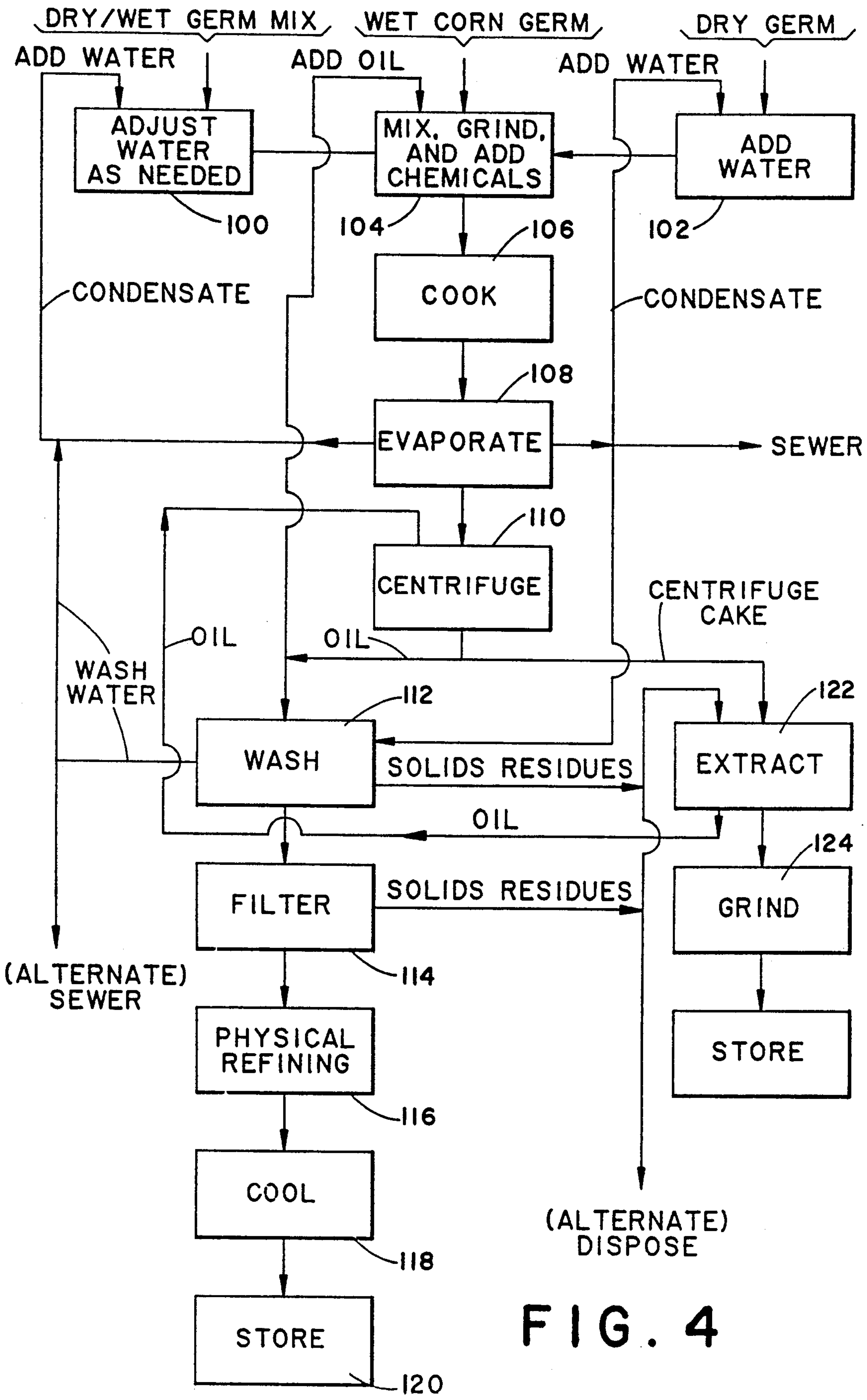

With reference to FIGS. 2 and 4, the subject invention as it is applicable to corn germ will be specifically discussed. With particular reference to FIG. 4, it may be seen that the invention is applicable to either a dry/wet corn germ mix, a wet corn germ, or a dry germ. The water level of the germ is adjusted as at 100, 102 to obtain a germ slurry which is properly cookable. Generally, the water level in the mixer should be at least 15% by weight. The oil and reagent chemicals are mixed and ground as at 104 to form a comminuted and homogenous slurry. The reagents comprise the same reagents which are used in the soybean processing illustrations. After the slurry has been agitated to achieve a thorough mixing, the slurry is heated or cooked as at 106 for a preselected period of time under a partial vacuum at a temperature no higher than approximately 99 degrees C. The cooking step accomplishes essentially the same results as the cooking step for the soybean processing, that is, rupturing of the calcium and magnesium bonds to render the non-hydratable phospholipids hydratable, lock-out of a reversion reaction as the water is evaporated, enzyme deactivation, pasteurization and protein insolubilization. After cooking, the slurry is subject to partial evaporation as at 108 and oil extraction as at 110 by centrifuge or a filter. The condensate from the evaporator can be either directed to a storage mixing tank or an oil product washing tank. The product oil from the centrifuge step 110 can be segregated into first and second portions. The first portion can be directed back to the slurry mixing tank. The second portion can be washed as at 112, filtered or centrifuged as at 114 to remove solids residue, physically refined as at 116, cooled as at 118 and stored as at 120 as a food quality oil. The cake from the centrifuging step 110 can be further processed as by extraction step 122 to remove a substantial portion of the residual oil. The press oil from the extraction step 122 can be conducted to the feed stream to the centrifuging step 110 to remove fines from the oil stream. The cake is subsequently comminuted and ground as at 124 and dried and stored as a meal product.

EXAMPLES FOR CORN OIL

Example No. 1

Four hundred grams (dry basis) of corn germ were taken from a wet milling process. Typically, the sample would contain 50% water, i.e. 800 grams of wet germ would contain 400 grams of dry germ and 400 grams of water. A dry sample of the germ would typically contain 45-50 weight percent of corn oil. Corn oil removed from the sample by means of extraction with a solvent such as hexane, typically had the following properties:

2.7% FFA 7.6 Red (Lovibond scale)

700 PPM of P

The four hundred grams ample of corn germ was mixed with 1200 ml of MAZOLA brand corn oil, a refined, bleached and deodorized corn oil, commercially available from CPC International Inc. of Englewood Cliffs, N.J. The approximate properties of the MAZOLA corn oil were as follows:

0.02% FFA 0.3 Red (Lovibond scale)

3 PPM of P

The slurry was introduced in the mixing and grinding container of a VITAMIX Super 3600 mixer (Note: The laboratory equipment used in this example is the same as described in the previous example for soybean). Three grams of concentrated (85%) phosphoric acid was added to the batch and the slurry was first mixed for two minutes at the lowest speed setting of the Vitamix. Subsequently, the slurry was ground for a period of ten minutes at the highest speed setting.

The mixed and ground slurry was then introduced in a flask. After the flask was sealed, a vacuum of approximately 29 inches of mercury (737 mm) was pulled on the flask. The water bath temperature was maintained at 95–100 degrees C.

The batch of ground corn germ and corn oil would boil at approximately 68–75 degrees C. and the temperature would remain level at approximately 68–75 degrees C. until substantially all of the water had been evaporated. At that point, the temperature would start to rise sharply and asymptotically approach the temperature of the water bath. When the slurry temperature reached approximately 85–90 degrees C., the vacuum was broken and the slurry sample was poured into a Buechner funnel lined with filter paper (Watman No. 5).

The filtered oil was collected in a flask. The oily filter cake, containing approximately 45–50 weight percent of oil was put in a press cage in which the ram of a Carver hydraulic laboratory press moved to compress the oily cake to a degree wherein the remaining press cake would only contain approximately 10 weight percent of residual oil. The oil separated from the cake was mixed with the filtered oil. A typical sample of the oil showed:

2.5% FFA 3.0 to 3.5 Red (Lovibond scale)

1 to 2 PPM of P

In each test 400 grams of corn germ (dry basis) was used containing approximately 200 grams of oil. As the press cake still contained 22 grams of oil at 10 weight percent residual oil content, the original MAZOLA corn oil sample was diluted with 178 grams of new oil originating from the corn germ. Thus, to replace the original MAZOLA corn oil sample of 1200 ml (or approximately 1,080 grams) required multiple tests similar to the one described above. Each test used 1200 ml of oil from the previous test. The test was repeated until the original MAZOLA sample had substantially disappeared and has been replaced by oil from the subsequent quantities of corn germ introduced. It was found in the series of tests that the free fatty acid content and the red color (Lovibond scale) would asymptotically approach the free fatty acid content and the red color of the oil in the germ, i.e. approximately 2.7 weight percent FFA and 3 to 3.5 Red. However, the phospholipid content of each subsequent oil sample would stay constant within a range of approximately 1 to 2 PPM measured as P. After approximately fifteen subsequent tests the FFA and Red color no longer varied. However, there was still no change of the phospholipid contents of the samples, which remained within the 1 to 2 PPM of P range.

In another series of runs, three grams of concentrated phosphoric acid reagent (85%) and 3 grams of sodium citrate reagent were added. Samples from these runs also showed 1 to 2 PPM of P.

The oil samples prepared were slightly cloudy. This cloudiness is generally attributed by those skilled in the art of producing corn oil to the presence of finely divided, dehydrated starch particles, which are carried with the corn germ, because existing processes for separating the corn germ from the corn starch cannot prevent typically 2 to 12 weight percent of starch from remaining with the germ.

A 1000 ml corn oil sample from a test was washed with 50 grams of distilled water. The wash solution was intensively mixed with the oil sample using the low speed setting of the VITAMIX mixer. After the mixing, the oil was centrifuged. A precipitate formed and the oil was no longer cloudy. The washed and decanted oil sample showed that substantially all phospholipids had been removed as the phosphorus content was judged to be in the 0 to 0.5 PPM range (AOCS Official Method Ca 12-55). Also, the sample did not show any detectable content of calcium, magnesium or iron and other trace metals.

Washing samples from other tests in the test series showed no statically significant departure of the test results from the earlier wash test, i.e. phospholipids measured as phosphorus were barely detectable (0 to 0.5 PPM range) and trace metals such as calcium, magnesium and iron could not be detected either.

Example No. 2

With reference to FIG. 2, a pilot plant 128 with a capacity of 2000 lbs./hr (908 kg/hr) of wet corn germ containing 50% of water by weight on the average was operated to produce high quality corn oil. The initial charge to the system was a semi-refined corn oil produced by CPC International Inc. with the following approximate properties: 0.25% FFA, FAC red 2 to 3, 20 PPM of P. The properties of the corn oil intrinsic to the corn germ used was as described in the previous example.

FIG. 2 shows the equipment of the pilot plant. A metering, variable speed screw conveyor 130 was calibrated to feed approximately 2000 lbs./hr (908 kg/hr) of wet germ to the system. The wet germ was introduced into a slurry preparation tank 132. This preparation tank 132 was partially filled with corn oil. At the initial start-up, the tank was filled to the required level from a tank containing the semi-refined oil described above. Once the plant was in operation, part of the oil separated in a centrifuge 134 and a screw press 136 was recycled to the slurry preparation tank 132 as discussed below. The quantity of oil in the slurry preparation tank 132 was maintained such that under steady state conditions a slurry composition of approximately 3.5 parts of oil by weight to 1 part of dry corn germ solids by weight was maintained. The slurry from the slurry preparation tank was pumped through a fixed hammer mill (not shown) of the type known as a Rietz disintegrator, which may be commercially obtained from Bepex Corporation of Minneapolis, Minn. This hammer mill typically sized the particles to a distribution of 10 weight percent +20 mesh, 82 weight percent +40 mesh.

The slurry with the sized particles was pumped to an evaporator 138. The temperature of the slurry feed was approximately 150 degrees F. (66 degrees C.); the feed rate was 2000 lbs./hr (908 kg/hr) of sized wet corn germ suspended in 3500 lbs./hr (1589 kg/hr) of oil (approximately 12 GPM or 54.6 liters per minute). The evaporator 138 was a single effect falling film evaporator. To maintain proper film formation in the tubes and good heat transfer conditions, the slurry in the evaporator 38 was recycled to the tube nest of the evaporator at a high rate of flow. The evaporator was operated with a vacuum of approximately 25 inches of mercury (735 mm) in the vapor space. Vapor temperature was approximately 150 degrees F. (66 degrees C.); the slurry temperature in the sump was maintained at 190–210 degrees F. (88–99 degrees C.) range. Slurry levels in the sump were maintained such that retention times of the slurry in the evaporator ranged from 10–30 minutes. The dried slurry from the evaporator sump was pumped to a horizontal decanter type centrifuge 134. For optimum separation of the solids in the centrifuge, 3–4 weight percent of moisture was maintained in the solids as measured on the basis of oil free solids. The oil content of the centrifuge cake was in the range of 35–55 weight percent. This centrifuge cake was subsequently pressed in the screw press 136 to separate substantially the balance of the oil. The oil remaining in the press cake was typically in the range of 4–6 weight percent. The oil from the press was added to the feed stream to the centrifuge 136 to separate solid fines which escaped with the oil through the oil discharge openings in the barrel of the press. The oil from the centrifuge flowed to a recycle tank 140 from where 3500 lbs./hr (1589 kg/hr) of oil was pumped back to the slurry preparation tank 132 to continue the process and 474 lbs./hr (215 kg/hr) of oil was pumped oil as product oil.

As the test runs proceeded, the initial charge of oil was replaced by an oil originating from the corn germ and the free fatty acid content would level out at approximately 2.7 to 3.0 percent by weight and the red color would approach 3 on the Lovibond scale.

In one series of test runs dilute sulfurous acid (approximately 0.1N) was added to the feed stream of the centrifuge at a rate of approximately 0.5 GPM (2.27 liters per minute). Oil samples were analyzed and showed approximately 6 PPM of P (phospholipids determined as P).

Approximately 5 lbs./hr (2.268 kg/hr) of 85% concentrated phosphoric acid was metered into the slurry preparation tank in another series of test runs. Oil samples from the centrifuge typically averaged 1 to 2 PPM of P.

In still another series of test runs 0.5 GPM (2.27 liters per minute) of a dilute phosphoric acid solution was injected in the centrifuge feed. This dilute solution was prepared by mixing 5 lbs (2.268 kg) of concentrated (85%) phosphoric acid into 250 lbs. (113.25 kg) of water. Oil samples taken from the centrifuge discharge showed an average of 4–8 PPM of P.

In another series of test runs 5 lbs./hr (2.268 kg/hr) of 85% concentrated phosphoric acid and 5 lbs./hr (2.268 kg/hr) of sodium citrate were added in the slurry preparation tank. Samples showed 1–22 PPM of P.

Oil samples from the three distinct series of runs were washed with distilled water. The oil samples measured 1000 ml. The wash water and the oil sample were intensely mixed in a Waring blender for a period of five minutes and then centrifuged. A sample taken from the centrifuged oil was filtered. The filtered sample showed no turbidity and the phosphorus content was judged to be less than 1 PPM of phosphorus. As before, the P content of the oils was measured according to AOCS Official Method Ca 12-55. This sample was also judged to be free of calcium, magnesium and iron.

The invention has been described with reference to the preferred embodiments. Obviously, modifications and alterations will occur to others upon the reading and understanding of the specifications. It is our intention to include all such modifications and alterations insofar as they come within the scope of the appended claims or the equivalents thereof.

What is claimed is:

1. A process for the extraction of a low phospholipid oil from an oil-bearing material which process comprises the steps of:

grinding the oil bearing material to leave ground oil-bearing material solids;

producing a slurry containing the oil-bearing material solids and a preselected reagent for substantially converting non-hydratable phospholipids in said solids into hydratable phospholipids;

heating the slurry for a predetermined time;

evaporating the slurry; and subsequently extracting a physically refinable oil from the solids, the phospholipids substantially remaining with the solids.

2. The process as claimed in claim 1 further including the step of mixing a sequestering agent with the ground oil-bearing material solids to prevent the reversion of the hydratable phospholipids into non-hydratable phospholipids.

3. The process as claimed in claim 1 wherein said preselected reagent is designed to reduce the phospholipid content of the oil to be extracted from the oil-bearing material.

4. The process as claimed in claim 3 wherein the preselected reagent is $H_3PO_4$.

5. The process as claimed in claim 3 wherein said preselected reagent is selected from the group consisting of $(CH_3CO)_2O$, $HOOCCH_2C(OH)$ $(COOH)—CH_2COOH—H_2O$, HCl, KCl, NaCl, NaOH, $Na_2HPO_4$, $KH_2PO_4$, $H_2SO_4$, $Na_2B_4O_7$ and $NH_2CH_2COOH$.

6. The process as claimed in claim 1 further comprising the steps of:

washing the extracted oil with water; and subsequently physically refining the washed, extracted oil.

7. The process as claimed in claim 1 wherein the oil-bearing material is selected from the group consisting of vegetable oil bearing seeds and plant material.

8. The process as claimed in claim 6 wherein the oil-bearing material is soybean or corn.

9. The process as claimed in claim 2 wherein the sequestering agent is $C_6H_5O_7Na_3—2H_2O$.

10. The process as claimed in claim 2 wherein the sequestering agent is selected from the group consisting of NaCl, $NaC_2H_3O_2$, $Na_2SO_4$, $NaHSO_4$, $Na_3PO_4$, $(HOOCCH_2)_2—NCH_2CH_2N(CH_2COOH)_2$, NaF, $Na_2C_2O_4$, $Na_2C_4H_4O_6—2H_2O$, $Na_2CO_3$ and $Na_4P_2O_7$.

11. The process of claim 1 wherein the step of extracting includes the steps of:

centrifuging the ground oil-bearing material solids for achieving an oil and solid phase separation.

12. A process for extracting a low phospholipid oil from a vegetable oil-bearing material, comprising the steps of:

grinding vegetable oil-bearing materials to produce ground vegetable oil-bearing solids;

preparing a slurry containing ground vegetable oil-bearing solids and a preselected reagent for converting non-hydratable phospholipids in the solids to hydratable phospholipids;

separating non-hydratable phospholipids from the vegetable oil-bearing materials to render the non-hydratable phospholipids into hydratable phospholipids;

mixing a sequestering agent with the ground vegetable oil-bearing solids to prevent the hydratable phospholipids from reverting into non-hydratable phospholipids;

cooking the slurry for a predetermined time;

evaporating the slurry; and subsequently extracting a physically refinable vegetable oil from the ground vegetable oil-bearing solids, the phospholipid substantially remaining with the solids.

13. The process as set forth in claim 12 wherein said preselected phospholipid-reducing reagent serves to reduce a phospholipid content of the oil to be extracted from the ground vegetable oil-bearing solids.

14. The process as set forth in claim 13 wherein said preselected phospholipid-reducing reagent is $H_3PO_4$.

15. The process as set forth in claim 13 wherein said preselected phospholipid-reducing reagent is selected from the group consisting of $(CH_3CO)_2O$, $HOOCCH_2$-$C(OH)$ $(COOH)$—$CH_2COOH$—$H_2O$, HCl, KCl, NaCl, NaOH, $Na_2HPO_4$, $KH_2PO_4$, $H_2SO_4$, $Na_2B_4O_7$ and $NH_2CH_2COOH$.

16. The process as set forth in claim 12 wherein the step of extracting includes subjecting the ground vegetable oil-bearing solids to centrifuging to promote an oil-solid phase separation.

17. The process as set forth in claim 12 comprising the additional step of:

subsequently physically refining the physically refinable oil.

18. The process as set forth in claim 12 wherein the sequestering agent is $C_6H_5O_7Na_3$—$2H_2O$.

19. The process as set forth in claim 12 wherein the sequestering agent is selected from the group consisting of NaCl, $NaC_2H_3O_2$, $Na_2SO_4$, $NaHSO_4$, $Na_3PO_4$, $(HOOCCH_2)_2$ $NCH_2CH_2N(CH_2COOH)_2$, NaF, $Na_2C_2O_4$, $Na_2C_4H_4O_6$—$2H_2O$, $Na_2CO_3$ and $Na_4P_2O_7$.

20. The process as set forth in claim 12 wherein the vegetable oil-bearing material is soybean or corn.

* * * * *